US008178660B2

(12) United States Patent
Weiner et al.

(10) Patent No.: US 8,178,660 B2
(45) Date of Patent: May 15, 2012

(54) VACCINES AND IMMUNOTHERAPEUTICS USING CODON OPTIMIZED IL-15 AND METHODS FOR USING THE SAME

(75) Inventors: David B. Weiner, Merion, PA (US); Michele Kutzler, Souderton, PA (US)

(73) Assignee: The Trustees of the University of Pennsylvania, Philadelpha ( * ) Notice: Subject to any disclaimer, the term of this patent is extended or adjusted under 35 U.S.C. 154(b) by 596 days.

(21) Appl. No.: 12/160,766

(22) PCT Filed: Jan. 12, 2007

(86) PCT No.: PCT/US2007/000886
§ 371 (c)(1),
(2), (4) Date: Mar. 30, 2009

(87) PCT Pub. No.: WO2007/087178
PCT Pub. Date: Aug. 2, 2007

(65) Prior Publication Data
US 2010/0003277 A1    Jan. 7, 2010

Related U.S. Application Data

(60) Provisional application No. 60/758,856, filed on Jan. 13, 2006.

(51) Int. Cl.
*C07H 21/02* (2006.01)
*C07H 21/04* (2006.01)
*A61K 48/00* (2006.01)

(52) U.S. Cl. ................ 536/23.1; 536/23.4; 536/23.5; 536/23.51; 514/44 R

(58) Field of Classification Search .................. None
See application file for complete search history.

(56) References Cited

U.S. PATENT DOCUMENTS

| | | | |
|---|---|---|---|
| 4,722,848 A | 2/1988 | Paoletti |
| 4,945,050 A | 7/1990 | Sanford |
| 5,017,487 A | 5/1991 | Stunnenberg |
| 5,036,006 A | 7/1991 | Sanford |
| 5,077,044 A | 12/1991 | Stocker |
| 5,110,587 A | 5/1992 | Paoletti |
| 5,112,749 A | 5/1992 | Brey |
| 5,174,993 A | 12/1992 | Paoletti |
| 5,223,424 A | 6/1993 | Cochran |
| 5,225,336 A | 7/1993 | Paoletti |
| 5,240,703 A | 8/1993 | Cochran |
| 5,242,829 A | 9/1993 | Panicali |
| 5,294,441 A | 3/1994 | Curtiss |
| 5,294,548 A | 3/1994 | McLinden |
| 5,310,668 A | 5/1994 | Ellis |
| 5,387,744 A | 2/1995 | Curtiss |
| 5,389,368 A | 2/1995 | Curtiss |
| 5,424,065 A | 6/1995 | Curtiss |
| 5,451,499 A | 9/1995 | Cochran |
| 5,453,364 A | 9/1995 | Paoletti |
| 5,462,734 A | 10/1995 | Letchworth, III et al. |
| 5,470,734 A | 11/1995 | Sondermeijer |
| 5,482,713 A | 1/1996 | Paoletti |
| 5,580,859 A | 12/1996 | Felgner |
| 5,593,972 A | 1/1997 | Weiner |
| 5,676,594 A | 10/1997 | Joosten |
| 5,703,055 A | 12/1997 | Felgner |
| 5,739,118 A | 4/1998 | Carrano |
| 5,817,637 A | 10/1998 | Weiner |
| 5,830,876 A | 11/1998 | Weiner |
| 5,962,428 A | 10/1999 | Carrano |
| 5,981,505 A | 11/1999 | Weiner |

FOREIGN PATENT DOCUMENTS

| | | |
|---|---|---|
| WO | WO 94/16737 | 8/1994 |
| WO | WO2004/059556 | 7/2004 |
| WO | WO2005/000235 | 1/2005 |
| WO | WO 2005/000235 | 1/2005 |
| WO | WO 2005/011874 A1 * | 12/2005 |

OTHER PUBLICATIONS

Howell, M.D. et al., Limited T-cell receptor beta-chain heterogeneity among interleukin 2 receptor-positive synovial T cells suggests a role for superantigen in rheumatoid arthritis, Proc. Natl. Acad. Sci. USA, 1991, 88:10921-10925.
Paliard, X. et al., Evidence for the effects of a superantigen in rheumatoid arthritis, Science, 1991, 253:325-329.
Williams, W.V. et al., Restricted heterogeneity of T cell receptor transcripts in rheumatoid synovium, J. Clin. Invest., 1992, 90:326-333.
Wucherpfennig, K.W. et al., Shared human T cell receptor V beta usage to immunodominant regions of myelin basic protein, Science, 1990, 248:1016-1019.
Oksenberg, J.R. et al., Limited heterogeneity of rearranged T-cell receptor V alpha transcripts in brains of multiple sclerosis patients, Nature, 1990, 345:344-346.
Chaudhary, V.K. et al., A rapid method of cloning functional variable-region antibody genes in *Escherichia coli* as single-chain immunotoxins, Proc. Natl. Acad. Sci. USA, 1990, 87:1066-1070.
Genbank Accession No. AF533540, Dec. 10, 2002.
Genbank Accession No. AF404757, Jul. 23, 2002.

(Continued)

*Primary Examiner* — Peter J Reddig
(74) *Attorney, Agent, or Firm* — Pepper Hamilton, LLP

(57) ABSTRACT

Nucleic acid molecules that encode IL-15 or fragments thereof, which express protein at a higher level than nucleic acid molecules with native coding sequences for IL-15 are disclosed. Nucleic acid molecules with additional modifications such as the absence of coding sequences for IL-15 signal sequences and/or the absence of IL-15 untranslated sequences and/or inclusion of non-IL-15 signal sequences are also disclosed. Vectors, including plasmids and viral vectors, comprising such nucleic acid molecules; and to host cells comprising such nucleic acid molecules are disclosed as well as methods of using such nucleic acid molecules alone or in combination with nucleic acid sequences encoding immunogens which are part of the nucleic acid molecules and/or part of a different nucleic acid molecule. Recombinant vaccines and live attenuated pathogens encoding fusion proteins, and methods of using the same, are disclosed.

31 Claims, 1 Drawing Sheet

OTHER PUBLICATIONS

Genbank Accession No. AF404756, Jul. 23, 2002.
Genbank Accession No. AF404755, Jul. 23, 2002.
Genbank Accession No. AF404754, Jul. 23, 2002.
Genbank Accession No. AF404753, Jul. 23, 2002.
Genbank Accession No. AF481864, May 21, 2002.
Genbank Accession No. M12294, May 8, 2002.
Genbank Accession No. AF317203, Nov. 28, 2008.
Genbank Accession No. AF196835, Dec. 7, 2000.
Genbank Accession No. AF260969, Aug. 27, 2000.
Genbank Accession No. AF260968, Aug. 27, 2000.
Genbank Accession No. AF260967, Aug. 27, 2000.
Genbank Accession No. AF206518, May 8, 2000.
Genbank Accession No. AF202541, Dec. 16, 1999.
Genbank Accession No. X14112, Oct. 23, 2008.
Hsu, Cary et al., "Primary human T lymphocytes engineered with a codon-optimized IL-15 gene resist cytokine withdrawal-induced apoptosis and persist long-term in the absence of exogenous cytokine", Journal of Immunology, 2005, 175:7226-7234.
Jalah, Rashmi et al., "Efficient systemic expression of bioactive IL-15 in mice upon delivery of optimized DNA expression plasmids", DNA and Cell Biology, 2007, 26:827-840.

* cited by examiner

SEQ ID NO:1

```
GAATTCGCCACCATGGACTGGACCTGGATCCTGTTCCTGGTGGCCGCCGCTACAAGAGTG
CACAGCAACTGGGTGAACGTGATCAGCGACCTGAAGAAGATCGAGGACCTGATCCAGAGC
ATGCACATCGACGCCACCCTGTACACCGAGAGCGATGTGCACCCCAGCTGTAAGGTGACC
GCCATGAAGTGCTTTCTGCTGGAGCTGCAGGTGATCAGCCTGGAGAGCGGCGACGCCAGC
ATCCACGACACCGTGGAGAACCTGATCATCCTGGCCAACAACAGCCTGAGCAGCAACGGC
AATGTGACCGAGAGCGGCTGTAAGGAGTGTGAGGAGCTGGAGGAGAAGAACATCAAGGAG
TTTCTGCAGAGCTTCGTGCACATCGTGCAGATGTTCATCAACACCAGCTGATGACTCGAG
```

VACCINES AND IMMUNOTHERAPEUTICS USING CODON OPTIMIZED IL-15 AND METHODS FOR USING THE SAME

CROSS-REFERENCE TO RELATED APPLICATIONS

This application is the U.S. National Stage filing of International Application Serial No. PCT/US2007/000886 filed Jan. 12, 2007, which claims priority to U.S. Provisional Patent Application No. 60/758,856, filed Jan. 13, 2006, each of which is incorporated herein by reference in its entirety.

FIELD OF THE INVENTION

The present invention relates to nucleic acid molecules that include a codon optimized nucleic acid sequence that encodes IL-15 and fragments thereof, improved vaccines, improved methods for prophylactically and/or therapeutically immunizing individuals against immunogens, and to improved immunotherapeutic compositions and improved immunotherapy methods.

BACKGROUND OF THE INVENTION

Immunotherapy refers to modulating a person's immune responses to impart a desirable therapeutic effect. Immunotherapeutics refer to those compositions which, when administered to an individual, modulate the individual's immune system sufficient to ultimately decrease symptoms which are associated with undesirable immune responses or to ultimately alleviate symptoms by increasing desirable immune responses. In some cases, immunotherapy is part of a vaccination protocol in which the individual is administered a vaccine that exposes the individual to an immunogen against which the individual generates an immune response. in such cases, the immunotherapeutic increases the immune response and/or selectively enhances a portion of the immune response (such as the cellular arm or the humoral arm) which is desirable to treat or prevent the particular condition, infection or disease.

Vaccines are useful to immunize individuals against target antigens such as allergens, pathogen antigens or antigens associated with cells involved in human diseases. Antigens associated with cells involved in human diseases include cancer-associated tumor antigens and antigens associated with cells involved in autoimmune diseases.

In designing such vaccines, it has been recognized that vaccines that produce the target antigen in cells of the vaccinated individual are effective in inducing the cellular arm of the immune system. Specifically, live attenuated vaccines, recombinant vaccines which use avirulent vectors, and DNA vaccines each lead to the production of antigens in the cell of the vaccinated individual which results in induction of the cellular arm of the immune system On the other hand, killed or inactivated vaccines, and sub-unit vaccines which comprise only proteins do not induce good cellular immune responses although they do induce a humoral response.

A cellular immune response is often necessary to provide protection against pathogen infection and to provide effective immune-mediated therapy for treatment of pathogen infection, cancer or autoimmune diseases. Accordingly, vaccines that produce the target antigen in cells of the vaccinated individual such as live attenuated vaccines, recombinant vaccines that use avirulent vectors and DNA vaccines are often preferred.

While such vaccines are often effective to immunize individuals prophylactically or therapeutically against pathogen infection or human diseases, there is a need for improved vaccines. There is a need for compositions and methods that produce an enhanced immune response.

Likewise, while some immunotherapeutics are useful to modulate immune response in a patient there remains a need for improved immunotherapeutic compositions and methods.

SUMMARY OF THE INVENTION

The present invention relates to nucleic acid molecules that comprises nucleic acid sequence that encodes IL-15 protein comprising SEQ ID NO:1 or a fragment thereof which encodes a functional fragment of IL-15.

The present invention relates to nucleic acid molecules comprising SEQ ID NO:1 or a fragment thereof which encodes a functional fragment of IL-15 that are free of coding sequence for an IL-15 signal sequence and/or free of IL-15 Kozak region and/or IL-15 5' untranslated region and/or IL-15 3' untranslated region and/or comprising a coding sequence for a non-IL-15 signal sequence.

The present invention relates to nucleic acid molecules that comprises nucleic acid sequence that encodes IL-15 protein comprising SEQ ID NO: 1 or a fragment thereof which encodes a functional fragment of IL-15 and further comprise coding sequence for an immunogen.

The present invention relates to compositions that comprise a nucleic acid molecule that comprises nucleic acid sequence comprising SEQ ID NO:1 or a fragment thereof which encodes a functional fragment of IL-15 and a nucleic acid molecule that comprises a nucleic acid sequence that encodes an immunogen.

The present invention further relates to methods of modulating an immune response in an individual comprising administering to said individual a nucleic acid molecule comprising SEQ ID NO:1 or a fragment thereof which encodes a functional fragment of IL-15.

The present invention further relates to recombinant vaccines that comprise a nucleic acid molecule comprising SEQ ID NO: 1 or a fragment thereof which encodes a functional fragment of IL-15.

The present invention relates to methods of inducing an immune response in an individual against an immunogen comprising administering to said individual a nucleic acid molecule comprising SEQ ID NO:1 or a fragment thereof which encodes a functional fragment of IL-15 as part or in combination a nucleic acid molecule that encodes an immunogen or in combination with an immunogen.

BRIEF DESCRIPTION OF THE DRAWINGS

FIG. 1 shows SEQ ID NO: 1.

DETAILED DESCRIPTION OF PREFERRED EMBODIMENTS

Definitions

As used herein the term "target protein" is meant to refer to peptides and protein encoded by gene constructs of the present invention that act as target proteins for an immune response. The terms "target protein" and "immunogen" are used interchangeably and refer to a protein against which an immune response can be elicited. The target protein is an immunogenic protein that shares at least an epitope with a protein from the pathogen or undesirable cell-type such as a cancer cell or a cell involved in autoimmune disease against which an immune response is desired. The immune response directed against the target protein will protect the individual against and/or treat the individual for the specific infection or disease with which the target protein is associated.

As used herein, the term "genetic construct" refers to the DNA or RNA molecules that comprise a nucleotide sequence that encodes a target protein or immunomodulating protein. The coding sequence includes initiation and termination signals operably linked to regulatory elements including a promoter and polyadenylation signal capable of directing expression in the cells of the individual to whom the nucleic acid molecule is administered.

As used herein, the term "expressible form" refers to gene constructs that contain the necessary regulatory elements operable linked to a coding sequence that encodes a target protein or an immunomodulating protein, such that when present in the cell of the individual, the coding sequence will be expressed.

As used herein, the term "sharing an epitope" refers to proteins that comprise at least one epitope that is identical to or substantially similar to an epitope of another protein.

As used herein, the term "substantially similar epitope" is meant to refer to an epitope that has a structure that is not identical to an epitope of a protein but nonetheless invokes a cellular or humoral immune response which cross reacts to that protein.

As used herein, the term "intracellular pathogen" is meant to refer to a virus or pathogenic organism that, at least part of its reproductive or life cycle, exists within a host cell and therein produces or causes to be produced, pathogen proteins.

As used herein, the term "hyperproliferative diseases" is meant to refer to those diseases and disorders characterized by hyperproliferation of cells.

As used herein, the term "hyperproliferative-associated protein" is meant to refer to proteins that are associated with a hyperproliferative disease.

As used herein the term "immunomodulating protein" refers to a protein that modulates the immune system of a person to whom the immunomodulating protein is delivered. Examples of immunomodulatory proteins include: IL-15, CD40L, TRAIL; TRAILrecDRC5, TRAIL-R2, TRAIL-R3, TRAIL-R4, RANK, RANK LIGAND, Ox40, Ox40 LIGAND, NKG2D, F461811 or MICA, MICB, NKG2A, NKG2B, NKG2C, NKG2E, NKG2F, CD30, CD153 (CD30L), Fos, c-jun, Sp-1, Ap1, Ap-2, p38, p65Rel,MyD88, IRAK, TRAF6, IkB, NIK, SAP K, SAP1, JNK2, JNK1B2, JNK1B1, JNK2B2, JNK2B1, JNK1A2, JNK2A1, JNK3A1, JNK3A2, NF-kappa-B2, p49 splice form, NF-kappa-B2, p100 splice form, NF-kappa-B2, p105 splice form, NF-kappa-B 50K chain precursor, NFkB p50, human IL-1 α, human IL-2, human IL-4, murine IL-4, human IL-5, human IL-10, human IL-15, human IL-18, human TNF-α, human TNF-β, human interleukin 12, MadCAM-1, NGF IL-7, VEGF, TNF-R, Fas, CD40L, IL4, CSF, G-CSF, GM-CSF, M-CSF, LFA-3, ICAM-3, ICAM-2, ICAM-1, PECAM, P150.95, Mac-1, LFA-1, CD34, RANTES, IL-8, MIP-1α, E-selecton, CD2, MCP-1, L-selecton, P-selecton, FLT, Apo-1, Fas, TNFR-1, p55, WSL-1, DR3, TRAMP, Apo-3, AIR, LARD, NGRF, DR4(TRAIL), DR5, KILLER, TRAIL-R2, TRICK2, DR6, ICE, VLA-1, and CD86 (B7.2).

Overview

The invention provides a nucleic acid sequence that encodes IL-15 which provides improved protein expression relative to the native sequence. The improved IL-15 coding sequence can be used in combination with the discoveries set forth in PCT application PCT/US04/18962 filed Jun. 14, 2004, U.S. Provisional Application No. 60/478,210 filed Jun. 13, 2003 and U.S. Provisional Application No. 60/478,205 filed Jun. 13, 2003, which are incorporated herein by reference, particularly those providing IL-15 protein coding sequences linked to non-IL-15 signal peptide, particularly IgE signal peptide, and the use of such constructs in vaccines and in constructs for delivery of IL-15 protein as an immunomodulating protein. In some preferred embodiments, the invention provides vectors, vaccines and immunomodulatory compositions and methods comprising nucleic acid molecules that comprise the nucleotide sequence of SEQ ID NO:1 or fragments thereof that encode functional fragments of IL-15. In some preferred embodiments, such nucleic acid molecules are provided free of coding sequences for IL-15 signal sequence, ands more preferably free of the IL-15 Kozak region and untranslated regions. In some preferred embodiments, the invention provides vectors, vaccines and immunomodulatory compositions and methods comprising nucleic acid molecules that comprise SEQ ID NO:1 or fragments thereof that encode functional fragments of IL-15 which are linked to coding sequences for human IgE signal sequence.

Native sequences that encode IL-15 have been modified to improve expression. In earlier improvements, elements such as coding sequences for IL-15 sequence and untranslated regions were deleted to improve expression. These earlier improvements may be incorporated and used in conjunction with the improved coding sequence of mature IL-15 protein set forth in SEQ ID NO:1. In preferred embodiments, the nucleic acid molecule that includes SEQ ID NO:1 is free of the coding sequence for IL-15 signal peptide, and preferably another signal protein such as IgE signal protein is provided in its place. Moreover, the IL-15 Kozak region and untranslated regions are removed as well to eliminate inhibitory elements. The only 11-15 sequences that constructs preferably include are the IL-15 sequences that encode the amino acid sequence of the mature IL-15 protein free of IL-15 signal peptide.

According to some embodiments, compositions are provided which comprise an isolated nucleic acid molecule comprising a nucleic acid sequence that encodes a fusion protein comprising a non-IL-15 signal sequence linked to IL-15 protein encoded by SEQ ID NO:1 or a fragment thereof that encodes a functional fragment of IL-15. In some preferred embodiments, the molecule is free of coding sequence for IL-15 signal sequence. In some preferred embodiments, the fusion protein is non-immunogenic in a human.

According to some embodiments, compositions are provided that include a nucleic acid construct comprising SEQ ID NO:1 or a fragment thereof that encodes a functional fragment of IL-15 and optionally the other earlier improvements described above may also include on the same nucleic acid molecule or a different nucleic acid molecule, a nucleic acid sequence that encodes an immunogen. Generally, immunogens, which are discussed below, may be any immunogenic protein including allergens, pathogen antigens, cancer-associated antigens or antigens linked to cells associated with autoimmune diseases. In preferred embodiments, the immunogen is a pathogen antigen, most preferably a pathogen selected from the group consisting of HIV, HSV, HCV, and WNV.

In some preferred embodiments, nucleic acid constructs are plasmids. In some preferred embodiments, the nucleic acid molecule is incorporated in a viral vector such as vaccinia, adenovirus, adenovirus associated virus, retrovirus, RSV, VSV, poxvirus or any other acceptable viral vector useful as a vaccine or gene therapy vector.

Genetic constructs comprising SEQ ID NO:1 or a fragment thereof that encodes a functional fragment of IL-15 may be incorporated directly into live attenuated pathogens according to some aspect of the invention. Examples of such pathogens useful as vaccines are set out below. In preferred embodiments, human IL-15, preferably free of IL-15 signal sequence, is linked to human IgE signal sequence.

Compositions that include coding sequences for immunogens are useful as vaccines. Compositions that do not include coding sequences for immunogens may be useful as immunomodulatory compositions. In some embodiments, protein immunogens, are also provided as a target for the immune response which will be enhanced by the expression of IL-15.

In some preferred embodiments, nucleic acid constructs are plasmids. In some preferred embodiments, the nucleic acid molecule is incorporated in a viral vector such as vaccinia, adenovirus, adenovirus associated virus, retrovirus, or any other acceptable viral vector useful as a vaccine or gene therapy vector.

Genetic constructs comprising SEQ ID NO:1 or a fragment thereof that encodes a functional fragment of IL-15 may be incorporated directly into live attenuated pathogens according to some aspects of the invention. Examples of such pathogens useful as vaccines are set out below. In preferred embodiments, human IL-15, preferably free of IL-15 signal sequence, is linked to human IgE signal sequence According to some embodiments of the invention, compositions of the invention comprise genetic constructs including coding sequences for immunogens and/or immunogenic proteins. Such compositions are delivered to an individual to modulate the activity of the individual's immune system and thereby enhance the immune response against the immunogen. When the nucleic acid molecules that encode an immunomodulatory protein are taken up by cells of the individual the nucleotide sequences that encode the immunomodulatory protein are expressed in the cells and the proteins are thereby delivered to the individual. Aspects of the invention provide methods of delivering the coding sequences of the proteins on a single nucleic acid molecule, in compositions comprising different nucleic acid molecules that encodes one or more of the various transcription factor or intermediate factors, as part of recombinant vaccines and as part of attenuated vaccines.

According to some aspects of the present invention, compositions and methods are provided which prophylactically and/or therapeutically immunize an individual against a pathogen or abnormal, disease-related cells. The vaccine may be any type of vaccine such as, a live attenuated vaccine, a cell vaccine, a recombinant vaccine or a nucleic, acid or DNA vaccine.

The present invention relates to compositions for delivering the immunomodulating proteins and methods of using the same.

The nucleic acid molecules may be delivered using any of several well known technologies including DNA injection (also referred to as DNA vaccination), recombinant vectors such as recombinant adenovirus; recombinant adenovirus associated virus and recombinant vaccinia.

DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

Routes of administration include, but are not limited to, intramuscular, intransally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include to mucosal tissue, intramuscular, intraperitoneal, intradermal and subcutaneous injection. Genetic constructs may be administered by means including, but not limited to, traditional syringes, needleless injection devices, or "microprojectile bombardment gene guns".

When taken up by a cell, the genetic construct(s) may remain present in the cell as a. functioning extracbromosomal molecule and/or integrate into the cell's chromosomal DNA. DNA may be introduced into cells where it remains as separate genetic material in the form of a plasmid or plasmids. Alternatively, linear DNA that can integrate into the chromosome may be introduced into the cell. When introducing DNA into the cell, reagents that promote DNA integration into chromosomes may be added. DNA sequences that are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation-signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal that is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode a target protein, the immunomodulating protein and, additionally, genes for proteins which further enhance the immune response against such target proteins. Examples of such genes are those which encode other cytokines and lymphokines such as alpha-interferon, gamma-interferon, platelet derived growth factor (PDGF), TNF, GM-CSF, epidermal growth factor (EGF), IL-1, IL-2, 11-4, IL-6, IL-10, IL-12 and IL-15 including IL-15 having the signal sequence deleted and optionally including the signal sequence from IgE.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells.

In some embodiments, gene constructs may be provided to in order to produce coding sequences for the immunomodulatory proteins described herein linked to IgE signal peptide.

One method of the present invention comprises the steps of administering nucleic acid molecules intramuscularly, intranasally, intraperatoneally, subcutaneously, intradermally, or topically or by lavage to mucosal tissue selected from the group consisting of inhalation, vaginal, rectal, urethral, buccal and sublingual.

In some embodiments, the nucleic acid molecule is delivered to the cells in conjunction with administration of a polynucleotide function enhancer or a genetic vaccine facilitator agent. Polynucleotide function enhancers are described in U.S. Ser. Nos. 5,593,972, 5,962,428 and International Application Serial Number PCT/US94/00899 filed Jan. 26, 1994, which are each incorporated herein by reference. Genetic vaccine facilitator agents are described in U.S. Ser. No. 021, 579 filed Apr. 1, 1994, which is incorporated herein by reference. The co-agents that are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with a GVF include growth factors, cytokines and lymphokines such as a-interferon, gamma-interferon, GM-CSF, platelet derived growth factor (PDGF), TNF, epidermal growth factor (EGF), ILA, IL-2, IL4, IL-6, IL-10, IL-12 and IL-15 as well as fibroblast growth factor, surface active agents such as immune-stimulating complexes (ISCOMS), Freunds incomplete adjuvant, LPS analog including monophosphoryl Lipid A (WL), muramyl peptides, quinone analogs and vesicles such as squalene and squalene, and hyaluronic acid may also be used administered in conjunction with the genetic construct In some embodiments, an immunomodulating protein may be used as a GVF. In some embodiments, the nucleic acid molecule is provided in association with PLG to enhance delivery/uptake.

The pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

According to some embodiments of the invention, methods of inducing immune responses against an immunogen are provided by delivering compositions of the invention to an individual. The vaccine may be a live attenuated vaccine, a cell vaccine, a recombinant vaccine or a nucleic acid or DNA vaccine.

In addition to using expressible forms of immunomodulating protein coding sequence to improve genetic vaccines, the present invention relates to improved attenuated live vaccines and improved vaccines that use recombinant vectors to deliver foreign genes that encode antigens. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 10 5,225,336; 5,240,703; 5,242,829; 5,294,441; 5,294,548; 5,310,668; 5,387,744; 5,389,368; 5,424,065; 5,451,499; 5,453,3 '64; 5,462,734; 5,470,734; and 5,482,713, which are each incorporated herein by reference. Gene constructs are provided which include the nucleotide sequence that encodes an immunomodulating protein is operably linked to regulatory sequences that can function in the vaccine to effect expression. The gene constructs are incorporated in the attenuated live vaccines and recombinant vaccines to produce improved vaccines according to the invention.

The present invention provides an improved method of immunizing individuals that comprises the step of delivering gene constructs to the cells of individuals as part of vaccine compositions which include are provided which include DNA vaccines, attenuated live vaccines and recombinant vaccines. The gene constructs comprise a nucleotide sequence that encodes an immunomodulating protein and that is operably linked to regulatory sequences that can function in the vaccine to effect expression. The improved vaccines result in an enhanced cellular immune response.

The present invention is useful to elicit enhanced immune responses against a target protein, i.e. proteins specifically associated with pathogens, allergens or the individual's own "abnormal" cells. The present invention is useful to immunize individuals against pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

According to some aspects of the present invention, DNA or RNA that encodes a target protein and immunomodulating proteins is introduced into the cells of tissue of an individual where it is expressed, thus producing the encoded proteins. The DNA or RNA sequences encoding the target protein and one or both immunomodulating proteins are linked to regulatory elements necessary for expression in the cells of the individual. Regulatory elements for DNA expression include a promoter and a polyadenylation signal. In addition, other elements, such as a Kozak region, may also be included in the genetic construct.

In some embodiments, expressible forms of sequences that encode the target protein and expressible forms of sequences that encode both immunomodulating proteins are found on the same nucleic acid molecule that is delivered to the individual.

In some embodiments, expressible forms of sequences that encode the target protein occur on a separate nucleic acid molecule from the nucleic acid molecules that contain expressible forms of sequences that encode one or more immunomodulatory proteins. In some embodiments, expressible forms of sequences that encode the target protein and expressible forms of sequences that encode one or more of the immunomodulatory proteins occur on a one nucleic acid molecule that is separate from the nucleic acid molecule that contain expressible forms of sequences that encode one or more of the immunomodulating proteins. Multiple different nucleic acid molecules can be produced and delivered according to the present invention and delivered to the individual. For example, in some embodiments, expressible forms of sequences that encode the target protein occur on separate nucleic acid molecule from the nucleic acid molecules that contain expressible forms of sequences that encode one or more of the two immunomodulating proteins which occur on separate nucleic acid molecule from the nucleic acid molecules that contain expressible forms of sequences that encode one or more immunomodulating proteins. In such cases, all three molecules are delivered to the individual.

The nucleic acid molecule(s) may be provided as plasmid DNA, the nucleic acid molecules of recombinant vectors or as part of the genetic material provided in an attenuated vaccine or cell vaccine. Alternatively, in some embodiments, the target protein and/or wither or both immunomodulating proteins maybe delivered as a protein in addition to the nucleic acid molecules that encode them or instead of the nucleic acid molecules which encode them.

Genetic constructs may comprise a nucleotide sequence that encodes a target protein or an immunomodulating protein operably linked to regulatory elements needed for gene expression. According to the invention, combinations of gone constructs that include one that comprises an expressible form of the nucleotide sequence that encodes a target protein and one that includes an expressible form of the nucleotide sequence that encodes an immunomodulating protein are provided. Incorporation into a living cell of the DNA or RNA molecule(s) that include the combination of gene constructs results in the expression of the DNA or RNA and production of the target protein and one or more immunomodulating proteins. An enhanced immune response against the target protein results.

The present invention may be used to immunize an individual against all pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhea, listeria and shigella. In addition, the present invention is also useful to immunize an individual against protozoan pathogens that include a stage in the life cycle where they are intracellular pathogens. Table 1 provides a listing of some of the viral families and genera for which vaccines according to the present invention can be made. DNA constructs that comprise DNA sequences that encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 2.

In order to produce a genetic vaccine to protect against pathogen infection, genetic material that encodes immunogenic proteins against which a protective immune response can be mounted must be included in a genetic construct as the coding sequence for the target. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The genetic construct used in the genetic vaccine can include genetic material that encodes many pathogen antigens. For example, several viral genes may be included in a single construct thereby providing multiple targets.

Tables 1 and 2 include lists of some of the pathogenic agents and organisms for which genetic vaccines can be prepared to protect an individual from infection by them. In some preferred embodiments, the methods of immunizing an individual against a pathogen are directed against HIV, HSV, HCV, WNV or HBV.

Another aspect of the present invention provides a method of conferring a protective immune response against hyperproliferating cells that are characteristic in hyperproliferative diseases and to a method of treating individuals suffering from hyperproliferative diseases. Examples of hyperproliferative diseases include all forms of cancer and psoriasis.

It has been discovered that introduction of a genetic construct that includes a nucleotide sequence which encodes—an immunogenic "hyperproliferating cell"-associated protein into the cells of an individual results in the production of those proteins in the vaccinated cells of an individual. To immunize against hyperproliferative diseases, a genetic construct that includes a nucleotide sequence that encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides; which comprise at least an epitope found on such proteins. In some cases, a hyperproliferative-associated protein is the product of a mutation of a gene that encodes a protein. The mutated gene encodes a protein that is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF. In addition to oncogene products as target antigens, target proteins for anti-cancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins that are found at higher levels in tumor cells including the protein recognized by monoclonal antibody 17-IA and folate binding proteins or PSA.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) that are involved in the disease have been characterized. These TCRs include $V\beta$-3, $V\beta$-14, $20V\beta$-17 and $V\alpha$-17. Thus, vaccination with a DNA construct that encodes at least one of these proteins will elicit an immune response that will target T cells involved in RA. See: Howell, M. D., et al., 1991 Proc. Nat. Acad. Sci. USA 88:10921-10925; Piliard, X., et al, 1991 Science 253:325-329; Williams, W. V., et al., 1992 J. Clin. Invest. 90:326-333; each of which is incorporated herein by reference. In MS, several specific variable regions of TCRs that are involved in the disease have been characterized. These TCRs include VfP and Va-10. Thus, vaccination with a DNA construct that encodes at least one of these proteins will elicit an immune response that will target T cells involved in MS. See: Wucherpfennig, K. W., et al., 1990 Science 248: 1016-1019; Oksenberg, J. R., et. al, 1990 Nature 345:344-346; each of which is incorporated herein by reference.

In scleroderma, several specific variable regions of TCRs that are involved in the disease have been characterized. These TCRs include $V\beta$-6, $V\beta$-8, $V\beta$-14 and $V\alpha$-16, $V\alpha$-3C, $V\alpha$-7, $V\alpha$-14, $V\alpha$-15, $V\alpha$-16, $V\alpha$-28 and $V\alpha$-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies that bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al 1987 Sequence of Proteins of Immunological Interest U.S. Department of Health and Human Services, Bethesda Md., which is incorporated herein by reference. In addition, a general method for cloning functional variable regions from antibodies can be found in Chaudhary, V. K., et al, 1990 Proc. Natl. Acad Sci. USA 87:1066, which is incorporated herein by reference.

The contents of the ASCII text file named SequenceLst-g.txt (5 KB in size), which was submitted to the United States Patent and Trademark Office on Jun. 22, 2011, in accordance with 37 CFR §§1.821-1.825, are incorporated by reference into the specification in their entirety.

TABLE 1

| | |
|---|---|
| Picornavirus Family Genera: | Rhinoviruses: (Medical) responsible for - 50% cases of the common cold. Etheroviruses: (Medical) includes polioviruses, coxsackieviruses, echoviruses, and human enteroviruses such as hepatitis A virus. Apthoviruses: (Veterinary) these are the foot and mouth disease viruses. |
| Target antigens: | VP1, VP2, VP3, VP4, VPG |
| Calcivirus Family Genera: | Norwalk Group of Viruses: (Medical) these viruses are an important causative agent of epidemic gastroenteritis. |
| Togavirus Family Genera: | Alphaviruses: (Medical and Veterinary) examples include Senilis viruses, RossRiver virus and Eastern & Western Equine encephalitis. Reovirug: (Medical) Rubella virus. |
| Flariviridue Family | Examples include: (Medical) dengue, yellow fever, Japanese encephalitis, St. Louis encephalitis and tick borne encephalitis viruses. West Nile virus (Genbank NC001563, AF533540, AF404757, AF404756, AF404755, AF404754, AF404753, AF481864, M12294, AF317203, AF196835, AF260969, AF260968, AF260967, AF206518 and AF202541) |
| Representative Target antigens: | E NS5 C Hepatitis C Virus: (Medical) these viruses are not placed in a family yet but are believed to be either a togavirus or a flavivirus. Most similarity is with togavirus family. |
| Coronavirus Family: (Medical and Veterinary) | Infectious bronchitis virus (poultry) Porcine transmissible gastroenteric virus (pig) Porcine hemaglutinating encephalomyelitis virus (pig) Feline infectious peritonitis virus (cats) Feline enteric coronavirus (cat) Canine coronavirus (dog) SARS associated coronavirus The human respiratory coronaviruses cause ~40 cases of common cold. EX. 224E, OC43 Note - coronaviruses may cause non-A, B or C hepatitis |
| Target antigens: | E1 - also called M or matrix protein E2 - also called S or Spike protein E3 - also called BE or hemagglutin-elterose glycoprotein (not present in all coronaviruses) N - nucleocapsid |
| Rhabdovirus Family Genera: | Vesiliovirus Lyssavirus: (medical and veterinary) rabies |
| Target antigen: | G protein N protein |
| Filoviridue Family: (Medical) | Hemorrhagic fever viruses such as Marburg and Ebola virus |
| Paramyxovirus Family: Genera: | Paramyxovirus: (Medical and Veterinary) Mumps virus, New Castle disease virus (important pathogen in chickens) Morbillivirus: (Medical and Veterinary) Measles, canine distemper Pneuminvirus: (Medical and Veterinary) Respiratory syncytial virus |
| Orthomyxovirus Family (Medical) | The Influenza virus |
| Bungavirus Family Genera: | Bungavirus: (Medical) California encephalitis, LA Crosse Phlebovirus: (Medical) Rift Valley Fever Hantavirus: Puremala is a hemahagin fever virus Nairvirus (Veterinary) Nairobi sheep disease Also many unassigned bungaviruses |
| Arenavirus Family (Medical) | LCM, Lassi fever virus |
| Reovirus Family Genera: | Reovirus: a possible human pathogen Rotavirus: acute gastroenteritis in children Orbiviruses: (Medical and Veterinary) Colorado Tick fever, Lebombo (humans) equine encephalosis, blue tongue |
| Retroyirus Family | |
| Sub-Family: | Oncorivirinal: (Veterinary) (Medical) feline leukemia virus, HTLVI and HTLVII Lentiviral: (Medical and Veterinary) HIV, feline immunodeficiency virus, equine infections, anemia virus Spumavirinal |

TABLE 1-continued

| | |
|---|---|
| Papovavirus Family | |
| Sub-Family: | Polyomaviruses: (Medical) BKU and JCU viruses |
| Sub-Family: | Papillomavirus: (Medical) many viral types associated with cancers or malignant progression of papilloma. Adenovirus (Medical) EX AD7, ARD., O.B. - cause respiratory disease - some adenoviruses such as 275 cause enteritis |
| Parvovirus Family (Veterinary) | Feline parvovirus: causes feline enteritis Feline panleucopeniavirus Canine parvovirus Porcine parvovirus |
| Herpesvirus Family | |
| Sub-Family: | alphaherpesviridue |
| Genera: | Simplexvirus (Medical) HSVI (Genbank X14112, NC001806), HSVII (NC001798) Varicellovinis: (Medical Veterinary) pseudorabies - varicella zoster |
| Sub-Family - | betaherpesviridue |
| Genera: | Cytomegalovirus (Medical) HCMV Muromegalovirus |
| Sub-Family. | Gammaherpesviridue |
| Genera: | Lymphocryptovirus (Medical) EBV - (Burkitts lympho) Rhadinovirus |
| Poxvirus Family | |
| Sub-Family: | Chordopoxviridue (Medical - Veterinary) |
| Genera: | Variola. (Smallpox) Vaccinia (Cowpox) Parapoxivirus - Veterinary Auipoxvirus - Veterinary Capripoxvirus Leporipoxvirus Suipoxviru's |
| Sub-Family: | Entemopoxviridue |
| Hepadnavirus Family | Hepatitis B virus |
| Unclassified | Hepatitis delta virus |

TABLE 2

| | |
|---|---|
| Bacterial pathogens | Pathogenic gram-positive cocci include: pneurnococcal; staphylococcal; and streptococcal. Pathogenic gram-negative cocci include: meningococcal; and gonococcal. Pathogenic enteric gram-negative bacilli include: enterobacteriaceae; *pseudomonas*, acinetobacteria and *eikenella*, melioidosis;, sahnonella; shigellosis; hemophilus; chancroid; brucellosis; tularemia; *yersinia (pasteurella)*; *streptobacillus mortiliformis* and *spirillum*; *listeria monocytogenes*; *erysipelothrix rhusiopathiae*; diphtheria, cholera, anthrax; donovanosis (granuloma inguinale); and bartonellosis. Pathogenic anaerobic bacteria include: tetanus; botulism; other clostridia; *tuberculosis*; leprosy; and other mycobacteria. Pathogenic spirochetal diseases include: syphilis; - treponematoses: yaws, pinta and endemic syphilis; and leptospirosis. Other infections caused by higher pathogen bacteria and pathogenic fungi include: actinomycosis;. nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma, and chromomycosis; and dermatophytosis. Rickettsial infections include rickettsial and rickettsioses. Examples of mycoplasma and chlarnydial infections include: *mycoplasma pneurnoniae*; lymphogranuloma venereum; psittacosis; and perinatal chlarnydial infections. |
| Pathogenic eukaryotes | Pathogenic protozoans and helminths and infections thereby include: amebiasis; malaria; leishmaniasis; trypanosomiasis; toxoplasmosis; *pneurnocystis carinii*; babesiosis; giardiasis; trichinosis; filariasis; schistosomiasis; nematodes; trematodes or flukes; and cestode (tapeworm) infections. |

The invention claimed is:

1. A nucleic acid molecule comprising SEQ ID NO: 1.

2. The nucleic acid molecule of claim 1 free of coding sequence for an IL-15 signal sequence.

3. The nucleic acid molecule of claim 1 free of IL-15 Kozak region and/or IL-15 5' untranslated region and/or IL-15 3' untranslated region.

4. The nucleic acid molecule of claim 1 comprising a coding sequence for a non-IL-15 signal sequence.

5. The nucleic acid molecule of claim 1 further comprising coding sequence for an immunogen.

6. The nucleic acid molecule of claim 5 wherein said immunogen is a pathogen antigen, or a cancer-associated antigen.

7. The isolated nucleic acid molecule of claim 6 wherein said immunogen is a pathogen antigen from a pathogen selected from the group consisting of HIV, HSV, HCV, and WNV.

8. The isolated nucleic acid molecule of claim 1 wherein said isolated nucleic acid molecule is a plasmid.

9. The nucleic acid molecule of claim 1 incorporated into a viral vector.

10. The nucleic acid molecule of claim 1 incorporated into a live attenuated pathogen.

11. A composition comprising a nucleic acid molecule of claim 1 and a nucleic acid molecule that comprises a nucleic acid sequence that encodes an immunogen.

12. The composition of claim 11 wherein said immunogen is a pathogen antigen, or a cancer-associated antigen.

13. The composition of claim 12 wherein said immunogen is a pathogen antigen from a pathogen selected from the group consisting of HIV, HSV, HCV, and WNV.

14. The composition of claim 11 wherein said nucleic acid molecules are plasmids.

15. An injectable pharmaceutical composition comprising the nucleic acid molecules as in any one of claims 1-3, 5-9 or the composition of claim 10.

16. A method of modulating an immune response in an individual comprising administering to said individual a nucleic acid molecule of claim 1, wherein the nucleic acid molecule is operably linked to a promoter and a polyadenylation signal.

17. A recombinant vaccine comprising a nucleic acid sequence that encodes an immunogen and a nucleic acid sequence of claim 1.

18. The recombinant vaccine of claim 17 wherein said immunogen is a pathogen antigen, or a cancer-associated antigen.

19. The recombinant vaccine of claim 18 wherein said immunogen is a pathogen antigen from a pathogen selected from the group consisting of HIV, HSV, HCV, and WNV.

20. The recombinant vaccine of claim 17 wherein said recombinant vaccine is a recombinant vaccinia vaccine.

21. A method of inducing an immune response in an individual against an immunogen comprising administering to said individual a nucleic acid molecule of claim 5, wherein the nucleic acid molecule is operably linked to a promoter and a polyadenylation signal.

22. A method of inducing an immune response in an individual against an immunogen comprising administering to said individual a composition of claim 11, wherein the nucleic acid molecules of claim 12 are operably linked to a promoter and a polyadenylation signal.

23. A method of inducing an immune response in an individual against an immunogen comprising administering to said individual a recombinant vaccine of claim 17, wherein the nucleic acids of claim 18 are operably linked to a promoter and a polyadenylation signal.

24. The nucleic acid molecule of claim 1 free of coding sequence for an IL-15 signal sequence and/or free of IL-15 Kozak region and IL-15 5' untranslated region and IL-15 3'untranslated region and comprising a coding sequence for a non-IL-15 signal sequence.

25. The nucleic acid molecule of claim 24 comprising a coding sequence for a non-IL-15 signal sequence operably linked to SEQ ID NO:1.

26. The nucleic acid molecule of claim 1 wherein the nucleic acid molecule is a plasmid.

27. The nucleic acid molecule of claim 5 free of coding sequence for an IL-15 signal sequence and/or free of IL-15 Kozak region and/or IL-15 5' untranslated region and/or IL-15 3'untranslated region.

28. The nucleic acid molecule of claim 27 comprising a coding sequence for a non-IL-15 signal sequence operably linked to SEQ ID NO:1.

29. The nucleic acid molecule of claim 4 wherein the nucleic acid molecule is a plasmid.

30. The composition of claim 11 wherein the nucleic acid molecule comprising SEQ ID NO: 1 is free of coding sequence for an IL-15 signal sequence and/or free of IL-15 Kozak region and/or IL-15 5' untranslated region and/or IL-15 3' untranslated region.

31. The composition of claim 30 wherein the nucleic acid molecule comprising SEQ ID NO: 1 comprises a coding sequence for a non-IL-15 signal sequence operably linked to SEQ ID NO:1.

* * * * *

SEQUENCE LISTING

<160> NUMBER OF SEQ ID NOS: 1

<210> SEQ ID NO 1
<211> LENGTH: 420
<212> TYPE: DNA
<213> ORGANISM: Artificial Sequence
<220> FEATURE:
<223> OTHER INFORMATION: human IL-15 variant

<400> SEQUENCE: 1

```
gaattcgcca ccatggactg gacctggatc ctgttcctgg tggccgccgc tacaagagtg      60
cacagcaact gggtgaacgt gatcagcgac ctgaagaaga tcgaggacct gatccagagc     120
atgcacatcg acgccaccct gtacaccgag agcgatgtgc accccagctg taaggtgacc     180
gccatgaagt gctttctgct ggagctgcag gtgatcagcc tggagagcgg cgacgccagc     240
atccacgaca ccgtggagaa cctgatcatc ctggccaaca acagcctgag cagcaacggc     300
aatgtgaccg agagcggctg taaggagtgt gaggagctgg aggagaagaa catcaaggag     360
tttctgcaga gcttcgtgca catcgtgcag atgttcatca acaccagctg atgactcgag     420
```